(12) United States Patent
Yoshida et al.

(10) Patent No.: US 7,993,662 B2
(45) Date of Patent: Aug. 9, 2011

(54) TRANSPARENT SOLID OIL COSMETICS

(75) Inventors: Mari Yoshida, Chiba (JP); Yuki Kokeguchi, Chiba (JP); Kiyoshi Maeno, Chiba (JP); Kiyotaka Kawai, Chiba (JP)

(73) Assignee: Kokyu Alcohol Kogyo Co., Ltd., Chiba (JP)

( * ) Notice: Subject to any disclaimer, the term of this patent is extended or adjusted under 35 U.S.C. 154(b) by 679 days.

(21) Appl. No.: 11/453,054

(22) Filed: Jun. 14, 2006

(65) Prior Publication Data

US 2006/0280763 A1    Dec. 14, 2006

Related U.S. Application Data

(60) Provisional application No. 60/788,257, filed on Mar. 31, 2006, provisional application No. 60/715,538, filed on Sep. 9, 2005.

(30) Foreign Application Priority Data

Jun. 14, 2005 (JP) .................................. 2005-200839
Jul. 29, 2005 (JP) .................................. 2005-243385

(51) Int. Cl.
*A61K 8/02* (2006.01)
(52) U.S. Cl. ........................................................ 424/401
(58) Field of Classification Search .................... None
See application file for complete search history.

(56) References Cited

U.S. PATENT DOCUMENTS

| | | | |
|---|---|---|---|
| 3,148,125 A | 9/1964 | Strianse et al. | |
| 5,981,680 A | 11/1999 | Petroff et al. | |
| 6,111,055 A | 8/2000 | Berger et al. | |
| 6,268,466 B1 | 7/2001 | MacQueen et al. | |
| 6,372,235 B1 * | 4/2002 | Livoreil et al. | 424/401 |
| 6,402,408 B1 | 6/2002 | Ferrari | |
| 6,960,339 B1 | 11/2005 | Ferrari | |
| 2003/0026772 A1 | 2/2003 | Jager-Lezer et al. | |
| 2003/0069388 A1 * | 4/2003 | Lawson et al. | 528/335 |
| 2003/0223943 A1 | 12/2003 | Uang et al. | |
| 2004/0170586 A1 | 9/2004 | Ferrari et al. | |
| 2005/0191327 A1 | 9/2005 | Yu et al. | |

FOREIGN PATENT DOCUMENTS

| | | |
|---|---|---|
| EP | 1 857 091 A1 | 11/2007 |
| JP | 64-090110 | 4/1989 |
| JP | 2001-039817 A | 2/2001 |
| JP | 2001-064514 | 3/2001 |
| JP | 2001-081320 | 3/2001 |
| JP | 2002332207 * | 5/2001 |
| JP | 2001-354543 A | 12/2001 |
| JP | 2002-516619 | 6/2002 |
| JP | 2002-534535 | 10/2002 |
| JP | 2003-113015 A | 4/2003 |
| JP | 2004-026711 A | 1/2004 |
| JP | 2004-131384 | 4/2004 |
| JP | 2004-131384 A | 4/2004 |
| JP | 2004-515510 | 5/2004 |
| JP | 2004-515515 | 5/2004 |
| JP | 2004-517907 | 6/2004 |
| WO | WO 02/47608 | 6/2002 |
| WO | WO 02/058643 | 8/2002 |
| WO | WO 2004066918 * | 1/2004 |
| WO | WO 2005/041917 A1 | 5/2005 |

* cited by examiner

*Primary Examiner* — Robert A Wax
*Assistant Examiner* — Danah Al-Awadi
(74) *Attorney, Agent, or Firm* — Wolf, Greenfield & Sacks, P.C.

(57) ABSTRACT

A solid cosmetic comprising components (A), (B), (C), and (D) below:
(A) a polyamide resin;
(B) diisostearyl malate;
(C) a polyglyceryl isostearate; and
(D) a liquid oil;
and not containing a wax when the component (A) comprises only an ester-terminated polyamide resin.

20 Claims, No Drawings

TRANSPARENT SOLID OIL COSMETICS

CROSS-REFERENCE TO RELATED APPLICATIONS

This application claims the benefit of U.S. Provisional Application Ser. No. 60/715,538, filed on Sep. 9, 2005 and U.S. Provisional Application Ser. No. 60/788,257, filed on Mar. 31, 2006.

FIELD OF THE INVENTION

The present invention relates to a transparent oil-based solid cosmetic that includes a polyamide resin, diisostearyl malate, a polyglyceryl isostearate, and a liquid oil.

BACKGROUND OF THE INVENTION

Transparent solid cosmetics containing a polyamide resin are conventionally known. For example, JP, B, 7-98731 discloses a transparent solid cosmetic containing a polyamide resin, a pentaerythritol rosinate ester, and a polyglycerol side-chain fatty acid partial ester or a polyglycerol unsaturated fatty acid partial ester.

In this publication, Versamid 930 (registered trademark, manufactured by Henkel Corp.), which is a thermoplastic condensate between a dimer acid and an alkylene polyamine such as ethylenediamine, diethylenediamine, or triethylenetetramine, and preferably has a molecular weight of 2000 to 10000 and a softening point of 70° C. to 100° C., is cited as an example of the polyamide resin.

JP, A, 2004-131384 discloses a transparent lipstick containing a polyamide gel formed from a fatty polyamide resin and an ester-terminated polyamide, multiple fatty acid esters in which a fatty acid has at least 6 carbon atoms in its carbon chain and a fatty alcohol has at least 3 carbon atoms in its carbon chain, and a fatty acid solute, which is contained at at least 1 wt % of the entirety of the components.

The polyamide having a terminal ester group described in this publication is an ester-terminated polyamide resin (ETPA).

JP, A, 2004-517907 describes a cosmetic composition containing at least one hetero polymer and at least one gelling agent, and a method for its use.

JP, A, 2004-515515 describes a transparent or translucent colored cosmetic composition for making up skin, lips, and an epidermal growing part, the composition containing a transparent or translucent cosmetic base and at least one type of coloring agent in an amount such that a 10 μm thick layer of a final composition has a transmittance of 20% to 80% when measured at the maximum wavelength of one of an absorption peak and a scattering peak of the coloring agent.

JP, A, 2002-534535 discloses a synthetic example and an application example of an amide-terminated polyamide resin (ATPA).

This publication describes the use of the ATPA in a personal care product and, in particular, a lipstick, etc. and also illustrates its structural formula and properties.

This publication also describes a synthetic example, the composition, and properties such as a softening point of the ATPA, which has the composition ethylenediamine: 60%, ditallowamine: 40%, etc. relative to dimer acid: 100% (mole equivalents %).

JP, A, 2002-516619 discloses a synthetic example and an application example of an ester-terminated polyamide resin (ETPA). This publication describes as a synthetic example an ETPA formed from components such as dimer acid: 100% (mole equivalents %), ethylenediamine: 65%, stearyl alcohol: 35%, etc. With regard to the ETPA of this synthetic example, the publication describes characteristic values such as a softening point (° C.) or a viscosity and also describes the use of a gel formed from this material and mineral oil in a hair care product, a personal care product, or a lipstick.

JP, A, 2004-515510 describes a lipstick composition containing isononanoic acid, isononylic acid, an ester-terminated polyamide resin, diisostearyl malate, and polyglyceryl-2 diisostearate, and containing a wax as a solid material.

JP, A, 2001-81320 describes a structured composition containing a liquid fatty phase that is structured by a polymer bonded to an amphiphilic compound having a specific HLB value. The publication states that in such a composition a liquid oil portion can be shaped into a stick form without employing a wax, and structuring can be carried out by the polymer without the composition being made opaque.

Furthermore, JP, A, 2001-64514 describes a composition that contains a continuous liquid fatty phase structured by a polyamide resin, the composition being in a solid configuration containing no wax, and in which a coloring material, the liquid fatty phase, and a polymer form a physiologically acceptable carrier.

SUMMARY OF THE INVENTION

The above-mentioned conventional solid cosmetics, particularly, the solid cosmetics used in lipsticks, are directed toward providing transparency, but none thereof has sufficient transparency. There is as yet no solid cosmetic that has adherence and spreadability and, in addition is not or little brittle and does not or hardly exude. Furthermore, there is no solid cosmetic that adequately has, in addition to the above-mentioned characteristics, various characteristics such as an appropriate hardness, ease of adhering to skin or hair during application, good spreading, no fading or discoloration, not bending when applied to the lips as a lipstick, imparting gloss, and vivid color of a colorant. There is therefore a strong desire for a solid cosmetic having sufficient transparency and the above-mentioned various characteristics.

It is therefore an object of the present invention to provide a solid cosmetic that can be shaped into a stick and has a transparency that surpasses conventional products. It is another object of the present invention to provide a colorless or colored solid cosmetic that is excellent in various characteristics such as practical characteristics (adhering during application, good spreadability, good durability (makeup lasting), glossy coated surface), appearance characteristics (high transparency), shape retention characteristics (appropriate hardness and bend strength, low brittleness), storage stability (small amount of exudation, transparency maintained, little fading, discoloration, or odor), and skin safety (no skin irritation), and which has transparency that surpasses conventional products.

The present inventors have found that a solid cosmetic having a high degree of transparency that has so far not been achievable can unexpectedly be obtained by using as a substrate a combination of a specified polyamide resin and a surfactant, and as a result of further intensive investigation the present invention has been accomplished.

That is, the present invention relates to
(1) a solid cosmetic comprising components (A), (B), (C), and (D) below:
(A) a polyamide resin;
(B) diisostearyl malate;
(C) a polyglyceryl isostearate; and
(D) a liquid oil;
and not containing a wax when the component (A) comprises only an ester-terminated polyamide resin.
(2) Furthermore, the present invention relates to the solid cosmetic, wherein the component (A) comprises an amide-terminated polyamide resin and/or an ester-terminated polyamide resin.
(3) Moreover, the present invention relates to the solid cosmetic, wherein the amide-terminated polyamide resin has the structure below.

[Chem. 1]

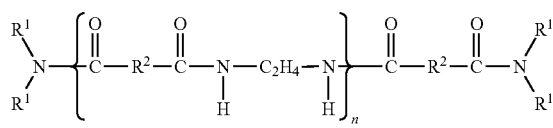

($R^1$: a straight chain or branched chain $C_8$ to $C_{22}$ alkyl group, $R^2$: a dimer acid residue or a dibasic acid residue, n=2 to 4)
(4) Furthermore, the present invention relates to the solid cosmetic, wherein the polyglyceryl isostearate is polyglyceryl-2 diisostearate.
(5) Moreover, the present invention relates to the solid cosmetic, wherein the liquid oil has a viscosity at 25° C. of 5 to 400 mPa·s and is one or more selected from a saturated liquid ester oil having a branched chain, squalane, and a hydrogenated polyisobutene.
(6) Furthermore, the present invention relates to the solid cosmetic, wherein the polyamide resin, diisostearyl malate, the polyglyceryl isostearate, and the liquid oil are contained at 5 to 50 mass %, 3 to 60 mass %, 3 to 60 mass %, and 3 to 60 mass % respectively.
(7) Moreover, the present invention relates to the solid cosmetic, wherein the content ratio of diisostearyl malate to the polyglyceryl isostearate is 1:10 to 10:1.
(8) Furthermore, the present invention relates to the solid cosmetic, wherein it further comprises as a component (E) at least one of a natural colorant, an oil-soluble dye, or a water-soluble dye.
(9) Moreover, the present invention relates to the solid cosmetic, wherein a 10 µm thick layer of the solid cosmetic has a maximum transmittance (%) for visible light (400 to 800 nm) of 90% or greater.
(10) Furthermore, the present invention relates to a lipstick comprising the solid cosmetic.
(11) Moreover, the present invention relates to a process for producing a solid cosmetic that includes components (A), (B), (C), and (D) below:
(A) a polyamide resin;
(B) diisostearyl malate;
(C) a polyglyceryl isostearate; and
(D) a liquid oil; the process comprising:
a step of selecting the solid cosmetic for which a layer thereof has a maximum transmittance (%) for visible light (400 to 800 nm) of a predetermined reference value or greater.

The solid cosmetic of the present invention employs a polyamide resin as a solidifying agent, and diisostearyl malate and a polyglyceryl isostearate, which have been found for the first time to have good solubility in the polyamide resin, as surfactants, and they are used in combination as a base. In accordance with such a constitution, the solid cosmetic of the present invention has solved the problem of opacity of the composition due to the addition of a polyamide resin and/or an oil, while maintaining the moldability required for a solid cosmetic.

Specifically, in order to solve the above-mentioned problems, the present inventors have paid attention to the miscibility of polyamide resins with various types of solvents and have carried out (1) a test with respect to the miscibility of known polyamide resins such as (a) "SYLVACLEAR A200V" (manufactured by Arizona Chemical Comp.) and (b) "SYLVACLEAR A2614V" (manufactured by Arizona Chemical Comp.), which are ATPAs, (c) "UNICLEAR 100VG" (manufactured by Arizona Chemical Comp.), which is an ETPA, and (d) Versamid 930 (manufactured by Cognis Deutschland GmbH & Co. KG.), which is neither an ATPA nor an ETPA, with various types of surfactants, dispersing agents, and liquid oils, and basic compositions for the transparent oil-based solid cosmetic have been selected (Tables 6 to 9).

Subsequently, the present inventors have paid attention to (2) the miscibility of various types of liquid oils with the basic composition of the transparent oil-based solid cosmetic, and have carried out tests with respect to the miscibility of the basic composition with various types of liquid oils and the transparency characteristics (Tables 10 to 17). Furthermore, the present inventors have prepared various types of solid cosmetics based on the results of the above tests, and have carried out tests with respect to various characteristics such as transparency, appearance characteristics, shape retention characteristics, application characteristics, storage stability, and skin safety of the cosmetics.

The solid cosmetic of the present invention has a much higher degree of transparency compared with conventional solid cosmetics.

Furthermore, among the solid cosmetics of the present invention, those in which the component (A) contains an amide-terminated polyamide resin and/or an ester-terminated polyamide resin have further superior transparency.

Moreover, among the solid cosmetics of the present invention, those in which the amide-terminated polyamide resin has the structure below have even further superior transparency.

[Chem. 2]

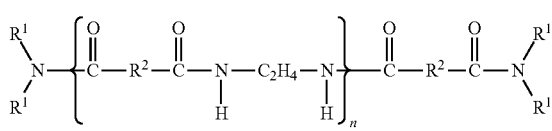

($R^1$: a straight chain or branched chain $C_8$ to $C_{22}$ alkyl group, $R^2$: a dimer acid residue or a dibasic acid residue, n=2 to 4)

Furthermore, among the solid cosmetics of the present invention,
those in which the polyglyceryl isostearate is polyglyceryl-2 diisostearate,
those in which the liquid oil has a viscosity at 25° C. of 5 to 400 mPa·s and is one or more types from a saturated liquid ester oil having a branched chain, squalane, and a hydrogenated polyisobutene, those in which the polyamide resin, diisostearyl malate, the polyglyceryl isostearate, and the liquid oil are contained at 5 to 50 mass %, 3 to 60 mass %, 3 to 60 mass %, and 3 to 60 mass % respectively, and those in which the content ratio of diisostearyl malate to the polyglyceryl isostearate is 1:10 to 10:1 are further superior in at least one of various characteristics such as appearance characteristics, shape retention characteristics (moldability, appropriate hardness as a solid cosmetic), application characteristics (lubrication, adherence, gloss, colorability when applied), storage stability (exudation, fading), and skin safety.

Moreover, among the solid cosmetics of the present invention, those containing as a component E at least one type of a natural colorant, an oil-soluble dye, and a water-soluble dye can impart a desired color to the solid cosmetic.

Furthermore, among the solid cosmetics of the present invention, those in which a 10 μm thickness of the solid cosmetic has a maximum transmittance (%) for visible light (400 to 800 nm) of at least 90% have very good transparency.

Moreover, a lipstick employing the solid cosmetic of the present invention not only has much higher transparency compared with conventional lipsticks and is therefore attractive, but since it is excellent in various characteristics such as appearance characteristics, shape retention characteristics, application characteristics, storage stability, and skin safety, it also has good applicability.

In accordance with the process for producing a solid cosmetic of the present invention, it is possible to reliably produce a solid cosmetic that is excellent in various characteristics such as appearance characteristics, shape retention characteristics, application characteristics, storage stability, and skin safety, and that has transparency that enhances the appearance of a product remarkably.

DETAILED DESCRIPTION OF THE INVENTION

The 'solid cosmetic' referred to in the present invention is a material that can maintain a solid form at normal temperature (about 25° C.) and can be used in a cosmetic such as a lipstick, a fragrance hair stick, or a hand stick.

The present invention is explained below in further detail.
Component (A)

The component (A) that can be used in the present invention is not particularly limited as long as it is a polyamide resin. Polyamide resins that can be used in the present invention include, according to the type of terminal group, an amide-terminated polyamide resin (ATPA), an ester-terminated polyamide resin (ETPA), etc., but are not limited thereto. Preferred polyamide resins are an amide-terminated polyamide resin and an ester-terminated polyamide resin, and the amide-terminated polyamide resin is particularly preferable.

The ATPA that is preferably used in the present invention is one represented by the formula below.

[Chem. 3]

$$R^1\underset{R^1}{\diagdown}N-\left[\underset{\|}{\overset{O}{C}}-R^2-\underset{\|}{\overset{O}{C}}-\underset{H}{N}-C_2H_4-\underset{H}{N}\right]_n\underset{\|}{\overset{O}{C}}-R^2-\underset{\|}{\overset{O}{C}}-N\underset{R^1}{\diagup}^{R^1}$$

($R^1$: straight chain or branched chain $C_8$ to $C_{22}$ alkyl groups, which may be identical to or different from each other, $R^2$: a dimer acid residue or a dibasic acid residue, n=2 to 4)

In the formula above, the $R^1$ groups are straight chain or branched chain alkyl groups; examples of the straight chain alkyl group include $C_8$: octyl, $C_{10}$: decyl, $C_{12}$: lauryl, $C_{14}$: myristyl, $C_{16}$: palmityl, $C_{18}$: stearyl, $C_{20}$: arachidyl, and $C_{22}$: behenyl. Examples of the branched chain alkyl group include $C_8$: 2-ethylhexyl, $C_9$: isononyl, $C_{10}$: isodecyl, $C_{13}$: isotridecyl, and $C_{18}$: isostearyl. Among them, $C_8$ to $C_{20}$ alkyl groups are preferable, $C_{14}$ to $C_{20}$ alkyl groups are more preferable, and $C_{14}$ to $C_{18}$ alkyl groups are the most preferable.

In the formula above, examples of $R^2$ include a dimer dilinoleic acid residue, which is a dimer acid residue, and residues of adipic acid, pimelic acid, suberic acid, azelaic acid, sebacic acid, undecane diacid, dodecane diacid, tridecane diacid, tetradecane diacid, pentadecane diacid, octadecane diacid, nonadecane diacid, and eicosane diacid, which are dibasic acids. Among them, the dimer dilinoleic acid residue is the most preferable.

Examples of the above-mentioned preferred ATPA include SYLVACLEAR A200V, A2614V (as the INCI Name, Ethylenediamine/Hydrogenated Dimer Dilinoleate Copolymer Bis-Di-$C_{14}$-$C_{18}$ Alkyl Amine), and examples of the ETPA include UNICLEAR 100VG (as the INCI Name, Ethylenediamine/Stearyl Dimer Tallate Copolymer), but the polyamide resin used in the present invention is not limited thereto. The structures of SYLVACLEAR A200V, A2614V, and UNICLEAR 100VG are as shown by the formulae below. General values for the physical properties of these resins are as described in Table 1.

ATPA details are described in JP, A, 2002-534535, and ETPA details are described in JP, A, 2002-516619.

Structure of SYLVACLEAR A200V, A2614V:

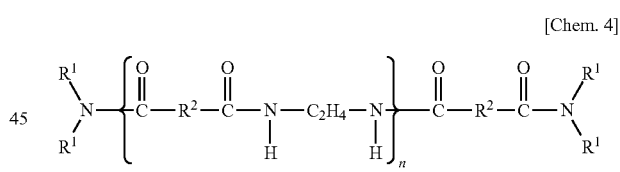

[Chem. 4]

($R^1$: a $C_{14}$ to $C_{18}$ alkyl amine group residue, $R^2$: a dimer dilinoleic acid residue, and n=2 to 4)

Structure of UNICLEAR 100VG

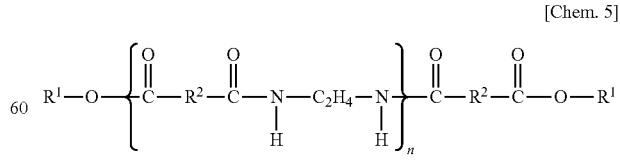

[Chem. 5]

($R^1$: a stearyl alcohol residue, $R^2$: a dimer dilinoleic acid residue, and n=3 to 4)

TABLE 1

Physical properties of each polyamide resin

|  | SYLVACLEAR A200V (high viscosity type) | SYLVACLEAR A2614V (low viscosity type) | UNICLEAR 100VG | Versamid 930 |
| --- | --- | --- | --- | --- |
| Molecular weight (Mn) | 3600 | 3000 | 3200 | — |
| Softening point (° C.) | 90-100 | 88-98 | 88-98 | 90-100 |
| Viscosity (cps/mPa · s) | 720 (110° C.) | 275 (110° C.) | 120 (160° C.) | 2100-2700 (160° C.) |
| Acid value | <15 | | <16 | — |
| Amine value | <2 | | <1 | — |

Versamid 930 is clearly different from SYLVACLEAR A200V and SYLVACLEAR A2614V, which are ATPAs, and UNICLEAR 100VG, which is an ETPA, in terms of components, structure, and characteristics (in particular, miscibility with an oil and a surfactant). Since an ATPA and an ETPA have their two terminals condensed with an alkyl amine (e.g. tallowamine) and an alkyl alcohol (e.g. stearyl alcohol), they have different characteristics from each other. Furthermore, an ATPA and an ETPA can be synthesized by appropriately adjusting target characteristic values such as molecular weight, softening point, and viscosity by changing the type and the reaction molar equivalent ratio of an alkylene polyamine and an alkyl amine or an alkyl alcohol relative to a dimer acid in the composition (ref. the above-mentioned structural formulae, Table 1, and a miscibility test described below).

The ATPA and ETPA contents are not limited, but from the viewpoint of transparency and structuring they are preferably 5 to 50 mass % of the entire solid cosmetic, more preferably 15 to 45 mass %, and most preferably 17 to 35 mass %.

The ATPA can be formed from (a-1) a high viscosity amide-terminated polyamide resin and (a-2) a low viscosity amide-terminated polyamide resin. The amount of (a-1) is preferably 3 to 40 mass %, more preferably 5 to 30 mass %, and most preferably 10 to 20 mass %. The amount of (a-2) is preferably 4 to 40 mass %, more preferably 5 to 35 mass %, and most preferably 15 to 25 mass %. The total amount of (a-1) and (a-2) is adjusted according to the type and the content of the other components and various desired characteristics for the solid cosmetic.

The solid cosmetic of the present invention may contain a wax. The 'wax' referred to in the present invention means an oleophilic fatty compound that maintains a solid form at normal temperature (about 25° C.). When component (A) is an ester-terminated polyamide only, however, the solid cosmetic does not contain a wax. Although a wax contributes to the moldability of the solid cosmetic, it can undesirably affect the transparency and gloss, which is the reason for the above.

Component (B) and Component (C)

Diisostearyl malate and the polyglyceryl isostearate of component (C) are agents that are miscible with component (A) and component (D), enhance transparency, suppress exudation, reduce brittleness, and function as solidifying agents (agents for maintaining and stabilizing solids). Both diisostearyl malate and the polyglyceryl isostearate are materials having a characteristic structure: They are carboxylic acid esters having an OH group.

A polyglycerol, which is a constituent component of component (C), is a polymer of glycerol, and although the degree of polymerization thereof is not limited, said degree is preferably 2 to 12, particularly preferably 2 to 10, and most preferably 2 to 3. Although the substitution number of side-chain isostearic acid, which is another constituent component of component (C), is not limited either, but it is preferably mono-substituted, di-substituted, or tri-substituted, particularly preferably di-substituted or tri-substituted, and it is most preferably di-substituted. Preferred examples of component (C) therefore include polyglyceryl-10 monoisostearate, polyglyceryl-10 diisostearate, polyglyceryl-10 triisostearate, polyglyceryl-2 monoisostearate, polyglyceryl-2 diisostearate, polyglyceryl-2 triisostearate, polyglyceryl-2 tetraisostearate, and polyglyceryl-3 diisostearate. Among them, polyglyceryl-2 diisostearate is the most preferable.

As shown in the evaluation of various characteristics illustrated in Examples, which will be described later, the combined use of component (B) and component (C) synergistically increases the transparency.

Although the content of component (B) is not limited, it is preferably 3 to 60 mass % relative to the entire solid cosmetic, more preferably 5 to 50 mass %, and most preferably 13 to 45 mass %.

The content of component (C) is not limited either, and it is preferably 3 to 60 mass % relative to the entire solid cosmetic, more preferably 5 to 50 mass %, and most preferably 17 to 45 mass %. The total content of component (B) and component (C) is not limited either, but it is preferably 6 to 70 mass %, more preferably 10 to 60 mass %, and most preferably 20 to 60 mass % (Table 22 and Table 24).

The content ratio of component (B) and component (C) is not limited, but it is preferably 1:10 to 10:1, more preferably 1:5 to 5:1, yet more preferably 3:7 to 5:5, and most preferably 1:2 to 2:1.

Component (D)

The 'liquid oil' referred to in the present invention is an oil phase that can maintain a liquid form at a room temperature of 25° C. and an atmospheric pressure of 760 mmHg, is formed from a single oil portion or a plurality of mutually miscible liquid oil portions that are liquid at room temperature, and means an oil phase, which is also called an oil.

Although the type of component (D) is not limited, but it is preferably at least one type selected from a saturated liquid ester oil having a branched chain, squalane, and a hydrogenated polyisobutene that have a viscosity of 5 to 400 (mPa·s) (Test Example 2). Among them, a more preferred liquid oil has a viscosity of 10 to 350 (mPa·s).

Although the content of component (D) is not limited, but it is preferably 3 to 60 mass % relative to the entire solid cosmetic, more preferably 5 to 50 mass %, and most preferably 10 to 30 mass %.

In the present invention, the ratio of the amount of component (D) relative to the sum of the amount of component (B) and the amount of component (C) ((D)/((B)+(C))) is preferably 0.08 to 5.5. By setting the above-mentioned ratio in such a range, a solid cosmetic having further superior transparency is obtained. That is, in the present invention, by optimizing the amount of surfactant relative to the liquid oil, which is a component impairing transparency, it is possible to further improve the transparency without degrading the moldability.

The value of (D)/((B)+(C)) is more preferably 0.6 to 2.3, and most preferably 1.0 to 2.0.

Component (E)

The 'coloring agent' referred to in the present invention means any known material that is commonly used in general cosmetics. Examples of the coloring agent include natural colorants such as shikonin, β-carotene, paprika, monascus, safflower red, safflower yellow, red cabbage color, purple sweet potato color, lycopene, cacao color, grape color, cochineal, lac color, beet red, and hematein.

Furthermore, Red. No. 215, Red. No. 218, Red. No. 223, Red. No. 225, Orange No. 201, Orange No. 206, Yellow No. 201, Green No. 202, and Purple No. 201, which are oil-soluble dyes, and Red. No. 2, Red. No. 3, Red. No. 102, Red. No. 104 (1), Red. No. 105 (1), Red. No. 106, Yellow No. 4, Yellow No. 5, Green No. 3, Blue No. 1, Blue No. 2, Red. No. 201, Red. No. 213, Red. No. 214, Red. No. 227, Red. No. 230 (1), Red. No. 230 (2), Red. No. 231, Red. No. 232, Orange No. 205, Orange No. 207, Yellow No. 202 (1), Yellow No. 202 (2), Yellow No. 203, Green No. 201, Green No. 204, Green No. 205, Blue No. 202, Blue No. 203, Blue No. 205, and Brown No. 201, which are water-soluble dyes, are also coloring agents that are used in the present invention.

Among these coloring agents, preferred examples of the coloring agent that have excellent antifading properties and solubility in the solid cosmetic of the present invention include natural colorants such as shikonin, β-carotene, paprika, lycopene, lac, and cochineal, oil-soluble dyes such as Red. No. 215, Red. No. 218, Red. No. 223, Red. No. 225, Orange No. 201, Green No. 202, and Purple No. 201, and water-soluble dyes such as Red. No. 3, Red. No. 102, Red. No. 104 (1), Red. No. 105 (1), Red. No. 106, Yellow No. 4, Green No. 3, Blue No. 1, Red. No. 201, Red. No. 213, Red. No. 230 (1), Orange No. 205, Yellow No. 202 (1), Green No. 204, and Blue No. 205. The content of these coloring agents is preferably 0.000001 to 10.0 mass % (pure content) of the entire solid cosmetic of the present invention, more preferably 0.00001 to 5.0 mass % (pure content), and most preferably 0.00005 to 3.0 mass % (pure content).

Diisostearyl malate, which is component (B), an ester of isostearic acid and polyglycerol, which is component (C), various type of ester oils, hydrocarbon squalane, and hydrogenated polyisobutene, which are used as component (D), are known materials and are readily available. The product name, abbreviation, INCI name, viscosity, supplier, etc. of these components are together given in Table 3, which is described later. With regard to the coloring agents, the product name and supplier of the natural colorants are given in Table 4, and the supplier and miscibility with the substrate of the transparent oil-based solid cosmetic are given in Table 5.

The 'having transparency' referred to in the present invention means that the solid cosmetic is not completely opaque. The transparency may be expressed by using as an indicator a maximum value (transparency) of the transmittance (%) of visible light (400 to 800 nm) with respect to a layer of the solid cosmetic.

The solid cosmetic of the present invention preferably has a maximum value of the transmittance (%) of at least 90% when evaluated at a thickness of 10 μm, more preferably has a maximum value of the transmittance (%) of at least 20% when evaluated at a thickness of 1 cm, and most preferably has a maximum value of the transmittance (%) of at least 30% when evaluated at a thickness of 1 cm.

The solid cosmetic of the present invention may be used in a lipstick, a color lipstick, a hand stick, a facial stick, a fragrance hair stick, etc. In particular, a lipstick containing the solid cosmetic of the present invention is preferable in terms of transparency and various other characteristics.

The process for producing a solid cosmetic of the present invention is a process for producing a solid cosmetic that includes components (A), (B), (C), and (D) below:

(A) a polyamide resin, (B) diisostearyl malate, (C) a polyglyceryl isostearate, and (D) a liquid oil, the process including a step of selecting the solid cosmetic for which a layer thereof has a maximum transmittance (%) for visible light (400 to 800 nm) of a predetermined reference value or greater. The reference value may be determined freely, but is preferably a value of 90% when evaluated at a thickness of 10 μm, more preferably a value of 20% when evaluated at a thickness of 1 cm, and most preferably a value of 30% when evaluated at a thickness of 1 cm. Other steps in the process for producing a solid cosmetic of the present invention may be carried out in accordance with a known process.

The present invention is explained below in further detail by reference to Test Examples and Examples.

Test Example 1

Miscibility of Polyamide Resin

A miscibility test was carried out using SYLVACLEAR A200V and SYLVACLEAR A2614V as ATPAs, UNICLEAR 100VG as an ETPA, and Versamid 930, which can be used in the present invention, with respect to the surfactants, ester oils, and hydrocarbons shown in Table 3. SYLVACLEAR A200V, SYLVACLEAR A2614V, and UNICLEAR 100VG are abbreviated to A200V, A2614V, and 100VG respectively.

Sample preparation method: a mixture of a polyamide resin (30 mass %), a surfactant (70 mass %), etc. was heated at a temperature of 100° C. to 120° C. and uniformly dissolved while stirring, then cooled to 80° C. to 90° C. while stirring, transferred to a pre-heated 50 mL glass container, stored in a temperature-controlled room at 45° C. for 1 hour, and then stored in a temperature-controlled room at 25° C. for at least 1 day. Evaluation results are given in Tables 6 to 9. Hereinafter, 'mass %' is abbreviated to % unless otherwise specified.

Evaluation Method for Various Characteristics (1) Evaluation of Transparency −1

Evaluation method for transparency: a sample such as a solid or an oil-based cosmetic was melted by heating, poured into a 1 cm thick methacrylate cell, and allowed to cool, the transmittance in the visible region (400 to 800 nm) was measured using a UV-160A spectrophotometer (manufactured by Shimadzu Corporation), and a control was prepared so as to have a maximum transmittance at a reference value. This control was used for evaluation of samples as shown in Table 2 using the criteria 'transparent', 'slightly cloudy', and 'cloudy' when visually examined, and the evaluation of each sample was expressed using 'A', 'B', or 'C'.

(2) Evaluation of Transparency −2

Evaluation at a thickness of 10 μm: a prepared sample was spread over a transparent slide so as to give a 10 μm thick layer, a value for the maximum transmittance (%) was obtained, and evaluation was carried out as shown in Table 2 (JP, A, 2004-515515).

TABLE 2

| Score | Evaluation of transparency –1 | | Evaluation of transparency –2 |
|---|---|---|---|
| | Evaluation criteria | Transmittance (%) | Transmittance (%) |
| A | Transparent | 30% or greater | 90% or greater |
| B | Slightly cloudy | at least 10% but less than 30% | at least 80% but less than 90% |
| C | Cloudy | less than 10% | less than 80% |

(3) Evaluation of Hardness

A sample such as a solid or an oil-based cosmetic was stored in a temperature-controlled room at 25° C. for at least 1 day, and measurement was carried out using an EZ-Test-20N hardness meter (manufactured by Shimadzu Corporation). The needle diameter was 1.0 mmφ, and the maximum value measured for the stress (N) at a needle penetration depth of 10 mm with a test speed of 10 mm/min was defined as the hardness.

(4) Exudation

After the sample stored in the 50 mL glass container as described in the above-mentioned sample preparation method was stored in a temperature-controlled room at 45° C. for 2 hours, the amount of exudation on the surface of the sample was visually evaluated. The extent to which the exudation went back when the sample was returned to the temperature-controlled room at 25° C. and stored for 3 hours was also evaluated. When the amount of exudation was small and there were no oil droplets, it was evaluated as 'A', when a slight degree of exudation was observed but the exudation went back in the temperature-controlled room at 25° C., it was evaluated as 'B', and when the amount of exudation was large and the exudation did not go back even in the temperature-controlled room at 25° C., it was evaluated as 'C'.

TABLE 3

| Product name | Abbreviation | INCI name | Viscosity (mPa·s/25° C.) | Supplier |
|---|---|---|---|---|
| Highmalate DIS | DIS | Diisostearyl malate | 2830 | *1 |
| Risorex PGIS21 | PGIS21 | Polyglyceryl-2 isostearate | 2430 | *1 |
| Risorex PGIS22 | PGIS22 | Polyglyceryl-2 diisostearate | 700 | *1 |
| Risorex PGIS23 | PGIS23 | Polyglyceryl-2 triisostearate | 330 | *1 |
| Risorex PGIS24 | PGIS24 | Polyglyceryl-2 tetraisostearate | 300 | *1 |
| Risorex PGIS32 | PGIS32 | Polyglyceryl-3 diisostearate | 3230 | *1 |
| KAK 98 | KAK 98 | Isononyl ethylhexanoate | 5 | *1 |
| KAK 99 | KAK 99 | Isononyl isononanoate | 6 | *1 |
| IPIS | IPIS | Isopropyl isostearate | 10 | *1 |
| ICEH | ICEH | Hexyldecyl ethylhexanoate | 11 | *1 |
| KAK 139 | KAK 139 | Isotridecyl isononanoate | 12 | *1 |
| KAK NDO | NDO | Neopentylglycol diethylhexanoate | 13 | *1 |
| CEH | CEH | Cetyl ethylhexanoate | 13 | *1 |
| Neolight 200P | 200P | Octyldodecyl neopentanoate | 15 | *1 |
| TOG | TOG | Triethylhexanoin | 35 | *1 |
| ISIS | ISIS | Isostearyl isostearate | 40 | *1 |
| KAK TTO | TTO | Trimethylolpropane triethylhexanoate | 52 | *1 |
| Risokasuta IOHS | IOHS | Ethylhexyl hydroxystearate | 64 | *1 |
| Risonol 24SP | 24SP | Decyltetradecanol | 80 | *1 |
| Risonol 28SP | 28SP | Dodecylhexadecanol | 40* | *1 |
| Risokasuta ODSHS | ODSHS | Octyldodecyl stearoyloxystearate | 90 | *1 |
| KAK PTO | PTO | Pentaerythrityl tetraethylhexanoate | 110 | *1 |
| KAK TTI | TTI | Trimethylolpropane triisostearate | 180 | *1 |
| TISG | TISG | Triisostearin | 185 | *1 |
| KAK PTI | PTI | Pentaerythrityl tetraisostearate | 290 | *1 |
| KAK DADIP-R | DIP-R | Diisopropyl dilinoleate | 310 | *1 |
| Risokasuta MIS | MIS | Hydrogenated castor oil isostearate | 950** | *1 |
| Risokasuta DA-L | DA-L | Hydrogenated castor oil dimer dilinoleate | 1400** | *1 |
| Highlucent ISDA | ISDA | (Polyglyceryl-2 isostearate/dimer dilinoleate) copolymer | 2500-3500** | *1 |
| Olive squalane | SQ | Squalane | 30 | *1 |
| Parleam 18 | PB | Hydrogenated polyisobutene | 340*** | *2 |
| EMix D | VE | Tocopherol | | *3 |

TABLE 3-continued

| Product name | Abbreviation | INCI name | Viscosity (mPa·s/25° C.) | Supplier |
|---|---|---|---|---|
| DC glitter gold I | Glitter G | (PET/Al/epoxy resin) laminate, iron oxide | | *4 |
| DC glitter silver C | Glitter S | (PET/Al/epoxy resin) laminate | | *4 |

Highlucent ISDA is a condensate formed from dimer acid, isostearic acid, and diglycerol described in JP, A, 2005-179377, and is an oligomer having a number-average molecular weight of 2000 to 7000 and a hydroxyl group value of 40 to 60.
Viscosity measurement temperature . . . *: 40° C., : 60° C., *: 100° C.
Supplier . . . *1: Kokyu Alcohol Kogyo Co., Ltd., *2: NOF Corporation, *3: Eisai Co., Ltd., *4: Diachemco Co., Ltd.

TABLE 4

| Natural colorant | Product name | Miscibility* | Supplier |
|---|---|---|---|
| Shikonin | Shikonin S | A | Maruzen Pharmaceuticals Co., Ltd. |
| Paprika | Paprika color DS-30B | A | Japan Chlorophyll Co., Ltd. |
| | Highorange RCL-10 | A | Daiwa Kasei Co., Ltd. |
| | Highorange WH | A | Daiwa Kasei Co., Ltd. |
| β-Carotene | MFC-β-carotene 300C | A | Mitsubishi-Chemical Foods Corporation |
| Monascus color | Daiwamonas L-150 | C | Daiwa Kasei Co., Ltd. |
| | Daiwamonas PH-3000 | C | Daiwa Kasei Co., Ltd. |
| Safflower yellow | Carthamus yellow | C | ALPS Pharmaceutical Ind. Co., Ltd. |
| | Safflower YL | C | Daiwa Kasei Co., Ltd. |
| | Safflower Y | C | Daiwa Kasei Co., Ltd. |
| Safflower red | Carthamus red All triturated powder | C | ALPS Pharmaceutical Ind. Co., Ltd. |
| Red cabbage color | Highred CR-N | B | Daiwa Kasei Co., Ltd. |
| Purple sweet potato color | Highred V80 | B | Daiwa Kasei Co., Ltd. |
| Lycopene | Lyc-O-Zone 1% | A | LycoRed |
| Cacao color | Os brown PN | B | Hodogaya Chemical Co., Ltd. Aizen Division |
| | Cacao color PN-LF | C | Hodogaya Chemical Co., Ltd. Aizen Division |
| Grape color | Red. No. G | B | Hodogaya Chemical Co., Ltd. Aizen Division |
| Cochineal color | Cochineal red AL | A | Daiwa Kasei Co., Ltd. |
| | Cochineal liquid 100 | A | ALPS Pharmaceutical Ind. Co., Ltd. |
| | OS cochineal red | C | Hodogaya Chemical Co., Ltd. Aizen Division |
| Lac color | Highred SL-NA | A | Daiwa Kasei Co., Ltd. |
| Beet red | Highred BL-O | A | Daiwa Kasei Co., Ltd. |
| Hematein | Hematein | C | Ichimaru Pharcos Co., Ltd. |
| Gardenia | Crocin P | C | ALPS Pharmaceutical Ind. Co., Ltd. |

*Prepared by heating and melting a sample formed from 0.2% of a coloring agent and 99.8% of a transparent oil-based solid cosmetic base (H-ATPA: 20%, L-ATPA: 5%, DIS: 25%, PGIS22: 25%, KAK139: 25%).
The evaluation method conforms to '(1) Miscibility evaluation method' above.

TABLE 5

| | Name of colorant | Miscibility* |
|---|---|---|
| Oil-soluble colorant | Red. No. 215 | A |
| | Red. No. 218 | A |
| | Red. No. 223 | A |
| | Red. No. 225 | A |
| | Orange No. 201 | A |
| | Yellow No. 201 | B |
| | Green No. 202 | A |
| | Purple No. 201 | A |
| Water-soluble colorant | Red. No. 2 | C |
| | Red. No. 3 | A |
| | Red. No. 102 | A |
| | Red. No. 104(1) | A |
| | Red. No. 105 | A |
| | Red. No. 106 | A |
| | Yellow No. 4 | A |
| | Yellow No. 5 | C |
| | Green No. 3 | A |
| | Blue No. 1 | A |
| | Blue No. 2 | — |
| | Red. No. 201 | A |
| | Red. No. 213 | A |
| | Red. No. 214 | — |
| | Red. No. 227 | B |
| | Red. No. 230(1) | A |
| | Orange No. 205 | A |
| | Yellow No. 202(1) | A |
| | Yellow No. 203 | C |
| | Green No. 201 | C |
| | Green No. 204 | A |
| | Blue No. 205 | A |
| | Brown No. 201 | C |

Supplier . . . Kishi Kasei Co., Ltd.

TABLE 6

| SYLVACLEAR A200V: 30% | | | |
|---|---|---|---|
| 70% | Transparency | Hardness | Exudation properties |
| DIS | A | 0.60 | A |
| PGIS21 | A | 0.35 | A |
| PGIS22 | A | 0.50 | A |
| PGIS23 | B | 0.58 | A |
| PGIS32 | A | 0.70 | A |
| IPIS | A | 0.65 | A |
| KAK139 | A | 0.65 | A |
| CEH | A | 0.60 | A |
| NDO | A | 0.95 | A |
| 200P | C | 0.50 | A |
| ICIS | C | 0.15 | A |
| TOG | C | 0.07 | A |
| ISIS | C | 0.10 | A |
| TTO | C | 0.03 | B |
| IOHS | A | 0.02 | B |
| PTO | C | 0.02 | B |
| TISG | C | 0.03 | B |
| TTI | C | 0.02 | B |
| PTI | C | 0.02 | B |

TABLE 6-continued

SYLVACLEAR A200V: 30%

| 70% | Transparency | Hardness | Exudation properties |
|---|---|---|---|
| 24SP | A | 0.05 | C |
| 28SP | A | 0.09 | C |
| SQ | C | 0.01 | A |
| PB | A | Paste | B |

TABLE 7

SYLVACLEAR A2614V: 30%

| 70% | Transparency | Hardness | Exudation properties |
|---|---|---|---|
| DIS | A | 0.12 | A |
| PGIS21 | A | 0.20 | A |
| PGIS22 | A | 0.13 | A |
| PGIS23 | A | 0.17 | A |
| CEH | A | 0.10 | A |
| NDO | A | 0.18 | A |
| TOG | B | 0.07 | B |
| TTO | C | 0.03 | B |
| PTO | C | 0.05 | B |
| TTI | C | 0.05 | B |
| PTI | C | 0.02 | B |
| SQ | C | Paste | A |
| PB | A | Paste | B |

TABLE 8

UNICLEAR 100VG: 30%

| 70% | Transparency | Hardness | Exudation properties |
|---|---|---|---|
| DIS | A | 0.80 | A |
| PGIS21 | A | 0.35 | A |
| PGIS22 | A | 0.33 | A |
| PGIS23 | B | 0.50 | A |
| IPIS | A | 0.60 | A |
| KAK139 | A | 0.50 | A |
| CEH | A | 0.70 | A |
| NDO | A | 0.90 | A |
| TOG | C | 0.06 | B |
| ISIS | C | 0.05 | B |
| PTO | C | 0.04 | B |
| TISG | C | 0.03 | B |
| TTI | C | 0.01 | B |
| PTI | C | 0.01 | B |
| SQ | C | 0.02 | A |
| PB | A | Paste | B |

TABLE 9

Versamid 930: 30%

| 70% | Transparency | Hardness | Exudation properties |
|---|---|---|---|
| DIS | C | 0.12 | A |
| PGIS22 | C | 3.00 | A |

From the evaluation results in Tables 6 to 9, (1) A200V and A2614V have excellent solubility in DIS and PGIS22, and although DIS easily causes brittleness, the transparency is high, and little exudation occurs. In addition, some of the ester oils have excellent solubility. (2) Versamid 930 has poor solubility in DIS and PGIS22, and the transparency is low. (3) With regard to the hardness, as a solution in DIS the hardness decreases in the order 100VG, A200V, A2614V, and Versamid 930, and as a solution in PGIS22 the hardness decreases in the order Versamid 930, A200V, 100VG, and A2614V.

Test Example 2

Miscibility of ATPA and ETPA with Surfactant and Liquid Oil

A test with respect to the miscibility of ATPA and ETPA with DIS, PGIS22, various types of ester oils, squalane, and hydrogenated polyisobutene was carried out. Sample compositions 1 to 64 were prepared as described below with the compositions shown in Tables 10 to Table 17, and evaluated, and the results are given in the tables.

Sample preparation method: Predetermined amounts (mass %) of all components were weighed, dissolved at a temperature of 100° C. to 110° C. as appropriate, stirred until uniform, then cooled to 80° C. to 90° C. while stirring, poured into a preheated 50 mL glass container, transferred to a temperature-controlled room at 45° C., stored for 1 hour while gradually cooling, further transferred to a temperature-controlled room at 25° C., and stored for at least 1 day, thus giving a sample.

Evaluation Methods for Various Characteristics
(1) Miscibility Evaluation Method
The miscibility at a temperature of 100° C. to 110° C. when preparing the sample was evaluated visually as a degree of difficulty. One that was easily miscible was evaluated as 'A', one that was slightly difficulty miscible was evaluated as 'B', and one that was difficulty miscible was evaluated as 'C'.
(2) Transparency Evaluation Method
Evaluation was carried out based on Table 2.

TABLE 10

| Physical properties | | | | | | | | | |
|---|---|---|---|---|---|---|---|---|---|
| | Molecular weight | Viscosity | 1 | 2 | 3 | 4 | 5 | 6 | 7 | 8 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | 28 | 38 | 28 | 38 | 28 | 38 | 28 | 38 |
| NDO | 356 | 13 | | | | | | | | |
| TOG | 422 | 35 | | | | | | | | |
| ISIS | 470 | 40 | | | | | | | | |
| PTO | 640 | 110 | | | | | | | | |
| TTI | 933 | 180 | | | | | | | | |
| SQ | 422 | 30 | | | | | | | | |
| PB | 1000 | 340* | | | | | | | | |
| Miscibility (100-110° C.) | | | A | A | A | A | A | A | A | A |
| Transparency (25° C.) | | | A | A | A | A | A | A | A | A |

Viscosity . . . mPa · s/25° C. (* mark indicates mPa · s/100° C.)

TABLE 11

| Physical properties | | | | | | | | | |
|---|---|---|---|---|---|---|---|---|---|
| | Molecular weight | Viscosity | 9 | 10 | 11 | 12 | 13 | 14 | 15 | 16 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | | | | | | | | |
| NDO | 356 | 13 | 28 | 38 | 28 | 38 | 28 | 38 | 28 | 38 |
| TOG | 422 | 35 | | | | | | | | |
| ISIS | 470 | 40 | | | | | | | | |

TABLE 11-continued

| | Physical properties | | | | | | | | | |
|---|---|---|---|---|---|---|---|---|---|---|
| | Molecular weight | Viscosity | 9 | 10 | 11 | 12 | 13 | 14 | 15 | 16 |
| PTO | 640 | 110 | | | | | | | | |
| TTI | 933 | 180 | | | | | | | | |
| SQ | 422 | 30 | | | | | | | | |
| PB | 1000 | 340* | | | | | | | | |
| Miscibility (100-110° C.) | | | A | A | A | A | A | A | A | A |
| Transparency (25° C.) | | | A | A | A | A | B | A | A | A |

TABLE 12

| | Physical properties | | | | | | | | | |
|---|---|---|---|---|---|---|---|---|---|---|
| | Molecular weight | Viscosity | 17 | 18 | 19 | 20 | 21 | 22 | 23 | 24 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | | | | | | | | |
| NDO | 356 | 13 | | | | | | | | |
| TOG | 422 | 35 | 28 | 38 | 28 | 38 | 28 | 38 | 28 | 38 |
| ISIS | 470 | 40 | | | | | | | | |
| PTO | 640 | 110 | | | | | | | | |
| TTI | 933 | 180 | | | | | | | | |
| SQ | 422 | 30 | | | | | | | | |
| PB | 1000 | 340* | | | | | | | | |
| Miscibility (100-110° C.) | | | A | A | A | A | A | A | A | A |
| Transparency (25° C.) | | | C | C | A | A | C | C | A | A |

TABLE 13

| | Physical properties | | | | | | | | | |
|---|---|---|---|---|---|---|---|---|---|---|
| | Molecular weight | Viscosity | 25 | 26 | 27 | 28 | 29 | 30 | 31 | 32 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | | | | | | | | |
| NDO | 356 | 13 | | | | | | | | |
| TOG | 422 | 35 | | | | | | | | |
| ISIS | 470 | 40 | 28 | 38 | 28 | 38 | 28 | 38 | 28 | 38 |
| PTO | 640 | 110 | | | | | | | | |
| TTI | 933 | 180 | | | | | | | | |
| SQ | 422 | 30 | | | | | | | | |
| PB | 1000 | 340* | | | | | | | | |
| Miscibility (100-110° C.) | | | A | A | A | A | A | A | A | A |
| Transparency (25° C.) | | | A | B | A | A | A | B | A | A |

TABLE 14

| | Physical properties | | | | | | | | | |
|---|---|---|---|---|---|---|---|---|---|---|
| | Molecular weight | Viscosity | 33 | 34 | 35 | 36 | 37 | 38 | 39 | 40 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | | | | | | | | |
| NDO | 356 | 13 | | | | | | | | |
| TOG | 422 | 35 | | | | | | | | |
| ISIS | 470 | 40 | | | | | | | | |
| PTO | 640 | 110 | 28 | 38 | 28 | 38 | 28 | 38 | 28 | 38 |
| TTI | 933 | 180 | | | | | | | | |
| SQ | 422 | 30 | | | | | | | | |
| PB | 1000 | 340* | | | | | | | | |
| Miscibility (100-110° C.) | | | A | A | A | A | A | A | A | A |
| Transparency (25° C.) | | | C | C | A | B | C | C | A | B |

TABLE 15

| | Physical properties | | | | | | | | | |
|---|---|---|---|---|---|---|---|---|---|---|
| | Molecular weight | Viscosity | 41 | 42 | 43 | 44 | 45 | 46 | 47 | 48 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | | | | | | | | |
| NDO | 356 | 13 | | | | | | | | |
| TOG | 422 | 35 | | | | | | | | |
| ISIS | 470 | 40 | | | | | | | | |
| PTO | 640 | 110 | | | | | | | | |
| TTI | 933 | 180 | 28 | 38 | 28 | 38 | 28 | 38 | 28 | 38 |
| SQ | 422 | 30 | | | | | | | | |
| PB | 1000 | 340* | | | | | | | | |
| Miscibility (100-110° C.) | | | A | C | A | A | A | C | A | A |
| Transparency (25° C.) | | | C | C | B | B | C | C | B | C |

TABLE 16

| | Physical properties | | | | | | | | | |
|---|---|---|---|---|---|---|---|---|---|---|
| | Molecular weight | Viscosity | 49 | 50 | 51 | 52 | 53 | 54 | 55 | 56 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | | | | | | | | |
| NDO | 356 | 13 | | | | | | | | |
| TOG | 422 | 35 | | | | | | | | |
| ISIS | 470 | 40 | | | | | | | | |
| PTO | 640 | 110 | | | | | | | | |
| TTI | 933 | 180 | | | | | | | | |
| SQ | 422 | 30 | 28 | 38 | 28 | 38 | 28 | 38 | 28 | 38 |
| PB | 1000 | 340* | | | | | | | | |
| Miscibility (100-110° C.) | | | A | A | A | A | A | A | A | B |
| Transparency (25° C.) | | | A | C | A | A | A | C | A | A |

TABLE 17

| | Physical properties | | | | | | | | | |
|---|---|---|---|---|---|---|---|---|---|---|
| | Molecular weight | Viscosity | 57 | 58 | 59 | 60 | 61 | 62 | 63 | 64 |
| A200V | | | 22 | 22 | 22 | 22 | | | | |
| 100VG | | | | | | | 22 | 22 | 22 | 22 |
| DIS | 639 | 2830 | 50 | 40 | | | 50 | 40 | | |
| PGIS22 | 699 | 700 | | | 50 | 40 | | | 50 | 40 |
| KAK 139 | 340 | 12 | | | | | | | | |
| NDO | 356 | 13 | | | | | | | | |
| TOG | 422 | 35 | | | | | | | | |
| ISIS | 470 | 40 | | | | | | | | |
| PTO | 640 | 110 | | | | | | | | |
| TTI | 933 | 180 | | | | | | | | |
| SQ | 422 | 30 | | | | | | | | |
| PB | 1000 | 340* | 28 | 38 | 28 | 38 | 28 | 38 | 28 | 38 |

TABLE 17-continued

| | Physical properties | | | | | | | | |
|---|---|---|---|---|---|---|---|---|---|
| Molecular weight | Viscosity | 57 | 58 | 59 | 60 | 61 | 62 | 63 | 64 |
| Miscibility (100-110° C.) | | A | A | A | A | A | A | B | B |
| Transparency (25° C.) | | B | B | A | A | B | B | A | A |

From the evaluation results shown in Tables 10 to 17, A200V had better miscibility with DIS, the high molecular weight ester oil, and the hydrocarbon oil than did 100VG. Furthermore, PGIS22 was generally better as a solvent than DIS.

Examples of the cosmetic of the present invention include a lipstick, a color lipstick, a hand stick, a facial stick, and a fragrance hair stick and so on, which have a transparent appearance.

The present invention is specifically explained below by reference to Examples, the present invention not being limited thereto: It is possible to appropriately add other surfactants, liquid oils, silicone oils, silicon derivatives, gelling agents, viscosity-increasing agents, antioxidants, coloring agents (dyes), pigments, pearl agents, glitter agents, preservatives, and moisturizing agents, which are normal cosmetic ingredients, in a range in which the object of the present invention can be achieved.

With regard to component (D) of the coloring agent-containing cosmetic of the present invention, a low viscosity ester oil, etc. is preferable since it functions as a solubilizing agent or a dispersant for the coloring agent. Furthermore, water, an ester, DPG, PG, a glycerol, etc. may be used if necessary as a solvent for the coloring agent in a range in which the object of the present invention can be achieved.

EXAMPLES

Transparent solid cosmetics of Examples 1 to 50 and Comparative Examples 1 to 6 were formed by the preparation method below, appearance characteristics, shape retention characteristics, application characteristics, storage stability, and skin safety were evaluated by the evaluation methods below, and the evaluation results of transparent lipsticks formed from the compositions of Tables 19 to 25 are given in the lower rows. In Examples 48 to 50, compositions were prepared from the ingredients for each cosmetic, they were evaluated in the same manner, and the evaluation characteristics are given in Table 29.

(1) Sample Preparation Method

Predetermined amounts (mass %) of all components were weighed, dissolved at a temperature of 100° C. to 110° C. as appropriate, stirred to give a uniform mixture, then injected into a normal lipstick-shaped mold (diameter 12.5 mm) or a stick-shaped mold (diameter 16.0 mm) at a temperature of 80° C. to 90° C., transferred to a temperature-controlled room at 45° C., gradually cooled over 1 hour, further transferred to a temperature-controlled room at 25°, and gradually cooled for 2 hours. The stick-shaped moldings were housed in a normal wind-out lipstick container or a stick-shaped mold container, then stored in a temperature-controlled room at 25° C. for at least 1 day, and subsequently subjected to each test.

(2) Appearance Characteristics (Evaluation of Transparency)

Evaluation was carried out based on Table 2.

(3) Shape Retention Characteristics

Samples obtained by the above-mentioned sample preparation method (1) were used.

(a) Hardness Evaluation

Measurement was carried out using an EZ-Test-20N hardness meter (manufactured by Shimadzu Corporation). The needle diameter was 1.0 mmφ, and the maximum value measured for the stress (N) at a needle penetration depth of 10 mm with a test speed of 10 mm/min was defined as the hardness.

(b) Break Strength

Measurement was carried out using the hardness meter used in the above-mentioned hardness measurement (a). The lipstick container or stick-shaped container was fixed horizontally, a load jig was attached to a side face of a wound-out stick at a position 10 mm from the end of a receiving plate of the stick (the base of the lipstick, etc.), and a load was applied under conditions of a stick temperature of 25° C. and a speed of 50 mm/min. The stress (N) at breakage was measured, and the maximum value was defined as the break strength. For the lipstick, a stick molded using a lipstick mold having a diameter of 12.5 mm was used, and for the others such as hand sticks, etc., a stick molded using a stick-shaped mold having a diameter of 16.0 mm was used.

(4) Application Characteristics

Samples of the Examples and Comparative Examples were subjected to a practical application test by 20 female panelists for one month, and evaluated. Evaluation items included 'adherence' and 'spreadability' when applying, 'durability (makeup lasting)', and 'gloss of coated surface'; an average value for each evaluation item was calculated, an evaluation of good, fair, or poor was expressed using a maximum number of points of 5 to a minimum of 0, and the average of these four evaluation items was further determined as an overall evaluation score. When the average of the evaluation scores was 3.5 to 5.0, it was denoted by 'A', when the average was 2.5 to 3.4, it was denoted by 'B', and when the average was 0 to 2.4, it was denoted by 'C'.

(5) Storage Stability

Samples of the Examples and Comparative Examples were stored in a temperature-controlled room at 40° C. for 3 months, then stored in a temperature-controlled room in which the temperature changed from −5° C. to 45° C. and then to −5° C. for a period corresponding to 5 cycles, and the presence or absence of exudation, separation, discoloration, odor, etc. were evaluated. The evaluation results were denoted by 'A' when they were good and no abnormality could be detected, 'B' when a slight abnormality could be detected with no problem in practice, and 'C' when they were bad and an abnormality could be detected.

(6) Skin Safety

A closed patch test of 0.05 g of a sample was carried out, using a 1.0 cm diameter circular patch test plaster with lint attached, on the skin of the forearm flexor area of each of 10 male subjects and 10 female subjects, that is, a total of 20, for 24 hours. The condition of the skin of each of the 20 subjects 1 hour and 24 hours after the plaster was removed was evaluated in accordance with the evaluation criteria below. Among the evaluations made 1 hour and 24 hours after the plaster was removed, that for which the reaction was more intense was employed; when 20 subjects showed (−), it was denoted by 'A', when 1 to 2 subjects showed (±), it was denoted by 'B', and when 3 or more subjects showed (±) or when one subject or more showed (+) to (+++), it was denoted by 'C'.

(Evaluation Criteria)

| (Skin conditions) | (Evaluation) |
|---|---|
| Erythema, swelling, vesicle | (+++) |
| Erythema, swelling | (++) |
| Erythema | (+) |
| Light erythema | (±) |
| No erythema, no swelling | (−) |

(7) Fading Evaluation (Sunlight Exposure Test)

The maximum transmittance ($T_0$ %) was measured before the test for each sample using a spectrophotometer.

The sample was left in a solar irradiation box (25° C.) for 10 days, 20 days, and 30 days, and the fading characteristics when irradiated (exposed) to sunlight for 8 hours/1 day in fine weather were evaluated.

The maximum transmittance ($T_{10}$, $T_{20}$, $T_{30}$) of samples exposed for 10 days, 20 days, and 30 days was determined. The change in transmittance over 10 days, $T_{10}$-$T_0$/$T_0$, was defined as a fading rate. Similarly, the fading rates $T_{20}$-$T_0$/$T_0$ and $T_{30}$-$T_0$/$T_0$ over 20 days and 30 days were calculated.

The evaluation criteria and the score were as described in Table 18.

Furthermore, in this invention, those evaluated as 'A' in the Examples did not show any change, such as fading, even when stored in a dark cool place for 1 year.

TABLE 18

| Score | Evaluation criteria | Change in transmittance (%) |
|---|---|---|
| A | Slightly faded in 30 days | Less than 10% |
| B | Slightly faded in 20 days | Less than 30% |
| C | Clearly faded in 10 days | 50% or greater |

As shown in Table 19, all of the solid cosmetics of the present invention had good transparency and no problem in their practical use. Furthermore, (1) an ester oil having a viscosity of less than 10 (mPa·s/25° C.) (e.g. KAK98, KAK99), exudation easily occurred, (2) an ester oil having a viscosity of 100 (mPa·s/25° C.) or greater (e.g. PTO, TTI), the adherence was a little poor but there were no problems in practice, and by using a liquid oil other than IOHS (ethylhexyl hydroxystearate) the exudation was further suppressed.

TABLE 20

| | | Example | | | | | |
|---|---|---|---|---|---|---|---|
| | | 10 | 11 | 12 | 13 | 14 | 15 |
| ATPA | A200V | 22.0 | 22.0 | 22.0 | 22.0 | 22.0 | 22.0 |
| | A2614V | | | | | | |
| DIS | | 15.0 | 15.0 | 15.0 | 15.0 | 15.0 | 15.0 |
| PGIS22 | | 40.0 | 40.0 | 40.0 | 40.0 | 40.0 | 40.0 |
| KAK139 | | | 11.5 | 11.5 | | | |
| KAK99 | | 10.0 | | | | | |
| NDO | | | | | 11.5 | 11.5 | 11.5 |
| TTI | | 13.0 | | | 11.5 | | |
| PTO | | | 11.5 | | 11.5 | | |
| PTI | | | | 11.5 | | | 11.5 |
| Transparency | | A | A | A | A | A | A |
| Hardness: 25° C. | | 0.21 | 0.22 | 0.23 | 0.22 | 0.20 | 0.22 |
| Break strength: 25° C. | | 0.80 | 1.00 | 1.00 | 0.80 | 1.00 | 0.90 |
| Application test | Adherence | A | A | A | A | B | B |
| | Spreadability | A | A | B | A | B | B |
| | Durability | A | A | A | A | A | A |
| | Gloss | A | A | A | A | A | A |
| Storage stability | | A | A | A | A | A | A |
| Skin safety | | A | A | A | A | A | A |

As shown in Table 20, all of the solid cosmetics of the present invention had good transparency. Furthermore, by employing as the liquid oil a mixture of a low viscosity ester oil (e.g. KAK99, NDO, KAK139) and a high viscosity ester oil (e.g. PTO, TTI, PTI), various characteristics was successfully improved.

TABLE 19

Type of ester oil

| | | Example | | | | | | | | | |
|---|---|---|---|---|---|---|---|---|---|---|---|
| | | 1 | 2 | 3 | 4 | 5 | 6 | 7 | 8 | 9 | 51 |
| ATPA | A200V | 22.0 | 22.0 | 22.0 | 22.0 | 22.0 | 22.0 | 22.0 | 22.0 | 22.0 | 22.0 |
| | A2614V | | | | | | | | | | |
| DIS | | 15.0 | 15.0 | 15.0 | 15.0 | 15.0 | 15.0 | 15.0 | 15.0 | 15.0 | 15.0 |
| PGIS22 | | 40.0 | 40.0 | 40.0 | 40.0 | 40.0 | 40.0 | 40.0 | 40.0 | 40.0 | 40.0 |
| KAK139 | | 23.0 | | | | | | | | | |
| KAK99 | | | 23.0 | | | | | | | | |
| KAK98 | | | | 23.0 | | | | | | | |
| IPIS | | | | | 23.0 | | | | | | |
| ISIS | | | | | | 23.0 | | | | | |
| ICEH | | | | | | | 23.0 | | | | |
| 200P | | | | | | | | 23.0 | | | |
| TOG | | | | | | | | | 23.0 | | |
| PTO | | | | | | | | | | 23.0 | |
| IOHS | | | | | | | | | | | 23.0 |
| Transparency | | A | A | A | A | A | A | A | A | A | A |
| Hardness: 25° C. | | 0.20 | 0.12 | 0.23 | 0.18 | 0.20 | 0.21 | 0.12 | 0.24 | 0.26 | 0.20 |
| Break strength: 25° C. | | 0.70 | 0.40 | 0.90 | 0.80 | 0.90 | 0.90 | 0.30 | 0.90 | 1.20 | 0.60 |
| Application test | Adherence | A | A | A | A | A | A | A | A | A | C |
| | Spreadability | A | A | A | A | A | A | A | A | A | A |
| | Durability | A | A | A | A | A | A | A | A | A | B |
| | Gloss | A | A | A | A | A | A | A | A | A | A |
| Storage stability | | A | A | A | A | A | A | A | A | A | C |
| Skin safety | | A | A | A | A | A | A | A | A | A | A |

TABLE 21

Extension of polyamide resin

| | | Example | | | | | | |
|---|---|---|---|---|---|---|---|---|
| | | 16 | 17 | 18 | 19 | 20 | 21 | 22 |
| ATPA | A200V | 15.0 | 20.0 | 22.5 | 25.0 | 30.0 | | |
| | A2614V | | | | | | 40.0 | 45.0 |
| | DIS | 5.0 | 50.0 | 22.5 | 10.0 | 15.0 | 5.0 | 5.0 |
| | PGIS22 | 30.0 | 10.0 | 25.0 | 40.0 | 40.0 | 50.0 | 5.0 |
| | KAK139 | 25.0 | | 25.0 | | 15.0 | | 40.0 |
| | KAK99 | 25.0 | 20.0 | | 10.0 | | 5.0 | |
| | TTO | | | | 5.0 | | | 5.0 |
| | PTI | | | 5.0 | | 5.0 | | |
| | Transparency | A | A | A | A | A | A | A |
| | Hardness: 25° C. | 0.12 | 0.27 | 0.26 | 0.34 | 0.35 | 0.25 | 0.34 |
| | Break strength: 25° C. | 0.40 | 0.90 | 1.00 | 1.10 | 1.30 | 0.90 | 1.10 |
| Appli- | Adherence | A | A | A | A | B | B | B |
| cation | Spreadability | A | A | A | A | B | B | B |
| test | Durability | A | A | A | A | A | A | A |
| | Gloss | A | A | A | A | A | A | A |
| | Storage Stability | B | A | A | A | A | B | A |
| | Skin safety | A | A | A | A | A | A | A |

As shown in Table 21, all of the solid cosmetics of the present invention had good transparency. Example 16 had a smaller amount of the high viscosity type A200V than those of Example 17, Example 18, Example 19, and Example 20, and contained none of the low viscosity type A2614V; the hardness was lower than that of the Examples above and Example 21 and Example 22, and the adherence and the spreadability were superior. When A200V is used on its own, the content thereof is preferably at most 30%.

TABLE 22

Mixture of high viscosity polyamide resin and low viscosity polyamide resin

| | | Example | | | | | | | | |
|---|---|---|---|---|---|---|---|---|---|---|
| | | 23 | 24 | 25 | 26 | 27 | 28 | 29 | 52 | 53 |
| ATPA | A200V | 20.0 | 20.0 | 15.0 | 10.0 | 5.0 | 10.0 | 5.0 | 15.0 | 25.0 |
| | A2614V | 5.0 | 10.0 | 15.0 | 20.0 | 25.0 | 30.0 | 35.0 | 5.0 | 15.0 |
| | DIS | 15.0 | 20.0 | 10.0 | 10.0 | 20.0 | 5.0 | 20.0 | 55.0 | 5.0 |
| | PGIS22 | 37.0 | 30.0 | 20.0 | 10.0 | 20.0 | 5.0 | 20.0 | 20.0 | 5.0 |
| | KAK139 | 23.0 | 20.0 | | 40.0 | | 40.0 | | | 50.0 |
| | KAK98 | | | 30.0 | | 20.0 | 10.0 | 20.0 | 5.0 | |
| | TOG | | | | 10.0 | | | | | 5.0 |
| | PTO | | | 10.0 | | 10.0 | | | | |
| | Transparency | A | A | A | A | A | A | A | A | A |
| | Hardness: 25° C. | 0.22 | 0.25 | 0.17 | 0.15 | 0.15 | 0.20 | 0.24 | 0.34 | 0.45 |
| | Break strength: 25° C. | 0.90 | 1.00 | 0.70 | 0.70 | 0.75 | 0.85 | 1.00 | 1.10 | 1.30 |
| Application | Adherence | A | A | A | A | A | A | B | B | C |
| test | Spreadability | A | A | A | A | A | A | B | C | C |
| | Durability | A | A | A | A | A | A | B | A | C |
| | Gloss | A | A | A | A | A | A | A | A | B |
| | Storage stability | A | A | B | B | B | A | A | C | A |
| | Skin safety | A | A | A | A | A | A | A | A | A |

As shown in Table 22, all of the solid cosmetics of the present invention had good transparency. In the Examples, the content of A200V and A2614V was 25% to 40%, and there were no particular problems in practical use.

In Examples 24 to 27, the content of A200V plus A2614V was 30%; when the proportion of A2614V increased, the hardness was reduced, but compared with this reduction, the break strength was maintained at a high level.

For example, in Example 28 and Example 29, the hardness increased due to an increase in the amount of A2614V, and it was confirmed that in the storage stability test the exudation characteristics were excellent.

In Comparative Examples 1 and 2, the values of (D)/((B)+(C)) were 0.067 and 5.5 respectively, and they had poorer adherence and spreadability than the solid cosmetics of the present invention.

TABLE 23

Use of A200V, A2614V, and 100VG

| | | Example | | | | | |
|---|---|---|---|---|---|---|---|
| | | 30 | 31 | 32 | 33 | 34 | 35 |
| ATPA | A200V | | | 10.0 | 5.0 | 5.0 | |
| | A2614V | | | | 5.0 | 10.0 | 40.0 |
| ETPA | 100V | 20.0 | 25.0 | 10.0 | 10.0 | 10.0 | 5.0 |
| | DIS | 15.0 | 40.0 | 15.0 | 15.0 | 15.0 | 10.0 |
| | PGIS22 | 40.0 | 15.0 | 40.0 | 45.0 | 35.0 | 20.0 |
| | KAK139 | 25.0 | 20.0 | 25.0 | | | 25.0 |
| | TISG | | | | 20.0 | 25.0 | |
| | Transparency | A | B | A | A | A | A |
| | Hardness: 25° C. | 0.23 | 0.25 | 0.23 | 0.25 | 0.30 | 0.30 |
| | Break strength: 25° C. | 0.80 | 0.90 | 0.90 | 0.90 | 1.00 | 1.00 |
| Application | Adherence | A | B | A | A | A | A |
| test | Spreadability | A | B | A | A | A | A |
| | Durability | A | B | A | A | A | A |
| | Gloss | A | A | A | A | A | A |
| | Storage stability | A | A | A | A | A | A |
| | Skin safety | A | A | A | A | A | A |

As shown in Table 23, all of the solid cosmetics of the present invention had good transparency. Compared with 100VG, the dependency of the hardness on the A200V content was smaller, and the brittleness was suppressed. Furthermore, as in the evaluation of Test Example 1 or Test Example 2 above, when ATPA and EPTA were used in combination, the miscibility with DIS and a high viscosity ester oil was excellent, and the composition had good transparency, adherence, and spreadability (Examples 30 and 32 to 35).

TABLE 24

Ratio of DIS and PGIS22

|  |  | Example | | | | Comparative Example | |
|---|---|---|---|---|---|---|---|
|  |  | 35 | 36 | 37 | 38 | 1 | 5 |
| ATPA | A200V | 20.0 | 20.0 | 20.0 | 22.0 | 22.0 | 22.5 |
|  | A2614V |  |  | 5.0 |  |  |  |
|  | DIS | 5.0 | 50.0 | 20.0 | 15.0 | 60.0 |  |
|  | PGIS22 | 50.0 | 5.0 | 30.0 | 40.0 | 0.0 | 1.3 |
|  | KAK139 | 25.0 | 20.0 | 25.0 | 20.0 | 18.0 | 76.2 |
|  | PTI |  | 5.0 |  | 3.0 |  |  |
| DIS/PGIS22 |  | 1/10 | 10/1 | 4/6 | 3/7 | 10/0 | 0/10 |
| Transparency |  | A | A | A | A | B | C |
| Hardness: 25° C. |  | 0.22 | 0.25 | 0.26 | 0.25 | 0.25 | 0.18 |
| Break strength: 25° C. |  | 0.90 | 0.90 | 1.20 | 0.90 | 1.10 | 0.5 |
| Application test | Adherence | A | B | A | B | C | B |
|  | Spreadability | B | B | A | A | B | B |
|  | Durability | A | A | A | B | B | B |
|  | Gloss | A | A | A | A | A | B |
| Storage stability |  | A | B | A | A | B | B |
| Skin safety |  | A | A | A | A | A | A |

As shown in Table 24, all of the solid cosmetics of the present invention had good transparency. Furthermore, when (B) DIS and (C) PSIS22 were used in combination, the amount of exudation was decreased, and the storage stability improved synergistically. Moreover, by adjusting the total content of (B) DIS and (C) PSIS22 so as to be in the range of 5% to 50%, the amount of exudation of a 'transparent lipstick' was reduced, and the storage stability improved. The total of (B) DIS and (C) PGIS22 is most preferably 20% to 60%. Furthermore, the content ratio of component (B) to component (C) is preferably (B):(C)=1:10 to 10:1, more preferably 1:5 to 5:1, yet more preferably 3:7 to 5:5, and most preferably 1:2 to 2:1. Furthermore, with regard to the miscibility of ATPA and ETPA with a surfactant and a liquid oil in Test Example 2 above (Tables 10 to 17), since the miscibility of (C) PGIS22 with each surfactant or liquid oil was superior to that of (B) DIS, the higher the proportion of PGIS22, the more preferable in some cases.

Comparative Examples 1 and 5, which contained no component (C) and no Component (B) respectively, had poorer transparency as well as poorer application characteristics, in particular, adherence, spreadability, and durability, compared with the solid cosmetics of the present invention.

TABLE 25

Addition of coloring agent

|  |  | Example | | | | | | | | | |
|---|---|---|---|---|---|---|---|---|---|---|---|
|  |  | 39 | 40 | 41 | 42 | 43 | 44 | 45 | 46 | 47 | 54 |
| ATPA | A200V | 22.5 | 20.0 | 22.5 | 22.5 | 22.5 | 22.5 | 20.0 | 20.0 | 20.0 | 20.0 |
|  | A2614V |  | 5.0 |  |  |  |  | 5.0 | 5.0 | 5.0 | 5.0 |
|  | DIS | 22.3 | 24.8 | 22.2 | 22.2 | 22.2 | 22.1 | 24.7 | 24.1 | 24.8 | 24.8 |
|  | PGIS22 | 22.5 | 20.0 | 22.5 | 22.5 | 22.5 | 22.5 | 20.0 | 20.0 | 25.0 | 25.0 |
|  | PGIS23 |  | 5.0 |  |  |  |  | 5.0 | 5.0 |  |  |
|  | KAK139 | 22.5 | 20.0 | 22.5 | 22.5 | 22.5 | 22.5 | 20.0 | 20.0 | 20.0 | 20.0 |
|  | ISDA | 5.0 |  |  |  |  | 5.0 | 5.0 |  |  |  |
|  | ODSHS |  |  | 5.0 |  | 5.0 |  |  | 5.0 |  |  |
|  | TOG |  | 5.0 |  | 5.0 |  |  |  |  |  |  |
|  | SQ |  |  | 5.0 |  | 5.0 |  |  |  | 5.0 |  |
|  | PTI | 5.0 |  |  | 5.0 |  | 5.0 |  |  |  | 5.0 |
| Coloring agent | Shikonin | 0.1 |  | 0.2 |  |  |  | 0.1 |  |  |  |
|  | Paprika color |  | 0.1 |  |  |  |  |  |  |  |  |
|  | β-Carotene |  | 0.1 |  | 0.1 |  |  |  | 0.1 |  |  |
|  | Lycopene | 0.1 |  |  |  |  | 0.1 |  |  |  |  |
|  | Red. No. 218 |  |  | 0.1 |  |  |  |  | 0.1 |  |  |
|  | Red. No. 223 |  |  |  |  |  |  |  |  | 0.1 |  |
|  | Orange No. 201 |  |  |  | 0.1 | 0.1 |  |  |  |  |  |
|  | Red. No. 104(1) |  |  |  |  | 0.2 |  |  |  |  |  |
|  | Red. No. 105(1) |  |  |  |  |  | 0.2 | 0.2 |  |  |  |
|  | Red. No. 201 |  |  |  |  |  |  |  | 0.1 |  |  |
|  | Red. No. 227 |  |  |  |  |  |  |  |  | 0.2 | 0.2 |
|  | Red. No. 202 |  |  |  |  |  |  |  |  |  | 0.2 |
|  | Glitter G |  |  |  |  |  |  | 0.5 |  |  |  |
| Transparency | Transparency-1 | A | A | A | A | A | A | A | — | B | B |
|  | Transparency-2 | A | A | A | A | A | A | A | — | A | A |
| Hardness: 25° C. |  | 0.26 | 0.27 | 0.26 | 0.26 | 0.26 | 0.26 | 0.27 | 0.27 | 0.27 | 0.27 |
| Break strength: 25° C. |  | 1.00 | 0.90 | 1.00 | 1.00 | 1.00 | 1.00 | 0.90 | 0.90 | 0.90 | 0.90 |
| Application test | Adherence | A | A | A | A | A | A | A | A | A | A |
|  | Spreadability | A | A | A | A | A | A | A | A | A | A |
|  | Durability | A | A | A | A | A | A | A | A | A | A |
|  | Gloss | A | A | A | A | A | A | A | A | A | A |
|  | Colorability | B | B | A | A | A | A | A | A | A | C |
| Storage stability |  | A | A | A | A | A | A | A | A | A | A |
| Skin safety |  | A | A | A | A | A | A | A | A | A | A |
| Fading |  | B | B | A | A | A | A | A | A | A | A |

As shown in Table 25, all of the solid cosmetics of the present invention had good transparency. The fading properties could be improved by the combined use of a natural colorant with an oil-soluble dye and a water-soluble dye (Example 41, Example 42, Example 44, Example 45).

Since Example 47 contained a pigment (Red. No. 202), it gave a plastic stick having an attractive red-colored appearance with a transparent feel and gloss.

In Examples 39 to 53, the water-soluble dye (Red. No. 227) had particularly excellent miscibility with the base. Example 54 had a composition similar to that of Example 37, and there were no problems with transparency or in its practical use.

Example 48

Transparent Hand Stick

TABLE 26

| | Ingredient | % |
|---|---|---|
| 1 | A200V | 18.0 |
| 2 | DIS | 16.9 |
| 3 | PGIS22 | 25.0 |
| 4 | PGIS21 | 10.0 |
| 5 | KAK139 | 25.0 |
| 6 | PB | 5.0 |
| 7 | VE | 0.1 |

Predetermined amounts of components 1 to 7 were measured, dissolved at a temperature of 100° C. to 110° C. as appropriate, stirred to give a uniform mixture, VE was added and stirred while gradually cooling, the mixture was injected into a normal stick-shaped mold (diameter 16.0 mm) at a temperature of 80° C. to 90° C., transferred to a temperature-controlled room at 45° C., gradually cooled over 1 hour, further transferred to a temperature-controlled room at 25° C., and gradually cooled for 2 hours. A stick-shaped molding was obtained, and was housed in a normal wind-out container.

Example 49

Transparent Facial Stick

TABLE 27

| | Ingredient | % |
|---|---|---|
| 1 | A2614V | 5.0 |
| 2 | A200V | 20.0 |
| 3 | DIS | 20.0 |
| 4 | PGIS22 | 15.0 |
| 5 | PGIS21 | 5.0 |
| 6 | ISIS | 22.0 |
| 7 | TTI | 6.0 |
| 8 | 24SP | 4.0 |
| 9 | 28SP | 3.0 |

Predetermined amounts of components 1 to 9 were measured, dissolved at a temperature of 100° C. to 110° C. as appropriate, stirred to give a uniform mixture, then injected into a normal mold (diameter 16.0 mm) at a temperature of 80° C. to 90° C., transferred to a temperature-controlled room at 45° C., gradually cooled over 1 hour, further transferred to a temperature-controlled room at 25° C., and gradually cooled for 2 hours. A stick-shaped molding was obtained, and was housed in a normal wind-out container. Components 8 and 9, which are additive components, are side chain-type fatty alcohols, and the spreadability (sliding) of the molding was improved.

Example 50

Transparent Fragrance Hair Stick

TABLE 28

| | Ingredient | % |
|---|---|---|
| 1 | A2614V | 10.0 |
| 2 | A200V | 20.0 |
| 3 | DIS | 10.0 |
| 4 | PGIS22 | 15.0 |
| 5 | PGIS32 | 4.0 |
| 6 | KAK139 | 24.5 |
| 7 | KAK99 | 10.0 |
| 8 | IOHS | 5.0 |
| 9 | Fragrance | 1.0 |
| 10 | Glitter S | 0.5 |

Predetermined amounts of components 1 to 10 were measured, dissolved at a temperature of 100° C. to 110° C. as appropriate, stirred to give a uniform mixture, mixed with a fragrance, stirred while gradually cooling, injected into a normal mold (diameter 16.0 mm) at a temperature of 80° C. to 90° C., transferred to a temperature-controlled room at 45° C., gradually cooled over 1 hour, further transferred to a temperature-controlled room at 25° C., and gradually cooled for 2 hours. A stick-shaped molding was obtained, and was housed in a normal wind-out container.

Glitter S (silver, particle size 0.1 to 0.2 mm), which is a glitter agent, was used. The solid thus obtained had an attractive appearance, having transparency with dispersed particles having a silver gloss.

Evaluation Results of Examples 48 to 50

TABLE 29

| | | Example 48 | Example 49 | Example 50 |
|---|---|---|---|---|
| | Transparency (25° C.) | A | A | A |
| | Hardness (25° C.) | 0.18 | 0.2 | 0.13 |
| Application test | Break strength (25° C.) | 1.6* | 1.8* | 1.5* |
| | Adherence | A | A | A |
| | Spreadability | A | A | A |
| | Durability | A | A | A |
| | Gloss | B | B | A |
| | Storage Stability | A | A | A |
| | Skin safety | A | A | A |

*Stick-shaped mold (diameter 16.0 mm)

Examples 48 to 50 employed moldings formed using a 16.0 mm mold. Increasing the diameter increases the break strength for samples having the same hardness. Furthermore, decreasing the content of IOHS enabled exudation to be suppressed (Examples 50 and 51).

Comparative Example 2

A composition (transparent lipstick) formed from the components below, which is described as an example of JP, A, 2004-131384, was prepared.

TABLE 30

| | Ingredient | % |
|---|---|---|
| 1 | UNICLEAR 100 | 40.0 |
| 2 | Isostearyl alcohol | 5.0 |
| 3 | Isostearic acid | 5.0 |
| 4 | Isopropylpalmitic acid salt* | 5.0 |
| 5 | Caprylic/capric acid triglyceride | 45.0 |

*Isopropylpalmitic acid ester in the original specification

This composition contained neither component B nor component C of the present invention, the hardness was as high as 0.45 N, the adherence and the spreadability were poor, and there was a problem with the moldability. Furthermore, when this composition was stored at high temperature, considerable exudation occurred in a short period of time, and it lacked practical usability as a lipstick.

Comparative Example 3

Compositions formed from the components described as Examples 1 and 2 respectively in JP, A, 2004-517907 were prepared.

TABLE 31

| | | Example 1 | | | | Example 2 | |
|---|---|---|---|---|---|---|---|
| | | Ingredient | % | | | Ingredient | % |
| Phase A | 1 | UNICLEAR 100 | 18.0 | Phase A | 1 | UNICLEAR 100 | 18.0 |
| | 2 | Isononyl isononanoate | 5.0 | Phase B | 2 | Bentone 38V | 3.0 |
| | 3 | Diisostearyl malate | 17.0 | | 3 | Diisostearyl malate | 16.3 |
| | 4 | Hydrogenated polybutene | 4.0 | | 4 | Isononyl isononanoate | 2.3 |
| Phase B | 5 | Hydrophobic silica (Aerosil R972) | 3.0 | | 5 | Hydrogenated polybutene | 36.4 |
| | 6 | Hydrogenated polybutene | 25.0 | | 6 | Hydrophobic silica (Aerosil R972) | 3.0 |
| | 7 | Isononyl isononanoate | 12.0 | Phase C | 8 | Pigment* | 7.0 |
| Phase C | 8 | Pigment* | 7.0 | | 9 | Isononyl isononanoate | 14.0 |
| | 9 | Hydrogenated polybutene | 9.0 | | | | |

As the pigment, Red. No. 202, which is commonly used as a lipstick component, was used.

These compositions contained no component C of the present invention, and were both in the form of a paste, and not only was it difficult to mold them, but also the spreadability was poor, and the feel was inferior.

Comparative Example 4

A composition (lipstick) formed from the components below, which is described in JP, A, 2004-515515, was prepared.

TABLE 32

| | Ingredient | % |
|---|---|---|
| 1 | UNICLEAR 100 | 25.0 |
| 2 | Octyldodecanol | 10.0 |
| 3 | Rocou* | 0.2 |
| 4 | Parleam oil | 64.8 |

Since Rocou (annatto) is difficult to obtain, Highorange WH (paprika colorant) having high transparency, which is of the same carotenoid colorant, was used as a substitute.

This composition contained no component B or component C of the present invention, and the transparency was good (in the transparency evaluation −1, the transmittance was 60%, (2) in the transparency evaluation −2, the transmittance was 75%, which transmittance was in the range of 20% to 80%), but it was difficult to mold, it was in the form of a paste, the spreadability was poor, and the feel was inferior.

The invention claimed is:

1. A solid cosmetic base consisting essentially of components (A), (B), (C), and (D) below:
   (A) a polyamide resin;
   (B) diisostearyl malate;
   (C) a polyglyceryl isostearate; and
   (D) a liquid oil;
   wherein a 10 μm thick layer of the solid cosmetic has a maximum transmittance (%) for visible light (400 to 800 nm) of 90% or greater.

2. The solid cosmetic base according to claim 1, wherein the component (A) comprises an amide-terminated polyamide resin and/or an ester-terminated polyamide resin.

3. The solid cosmetic base according to claim 2, wherein the amide-terminated polyamide resin has the structure below

[Chem. 1]

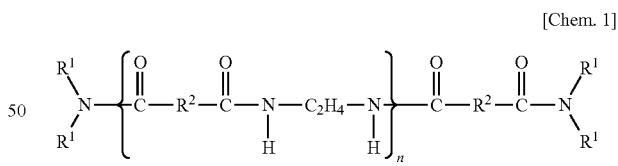

($R^1$: a straight chain or branched chain $C_8$ to $C_{22}$ alkyl group, $R^2$: a dimer acid residue or a dibasic acid residue, n=2 to 4).

4. The solid cosmetic base according to claim 1, wherein the polyglyceryl isostearate is polyglyceryl-2 diisostearate.

5. The solid cosmetic base according to claim 1, wherein the liquid oil has a viscosity at 25° C. of 5 to 400 mPa·s and is one or more selected from a saturated liquid ester oil having a branched chain, squalane, and a hydrogenated polyisobutene.

6. The solid cosmetic base according to claim 1, wherein the polyamide resin, diisostearyl malate, the polyglyceryl isostearate, and the liquid oil are contained at 5 to 50 mass %, 3 to 60 mass %, 3 to 60 mass %, and 3 to 60 mass % respectively.

7. The solid cosmetic base according to claim 1, wherein the content ratio of diisostearyl malate to the polyglyceryl isostearate is 1:5 to 5:1.

8. A solid cosmetic comprising the solid cosmetic base according to claim 1, and at least one component selected from the group consisting of a natural colorant, an oil-soluble dye, and a water-soluble dye.

9. A solid cosmetic comprising the solid cosmetic base according to claim 1.

10. A process for producing a solid cosmetic base, said solid cosmetic base consisting essentially of components (A), (B), (C), and (D) below:
(A) a polyamide resin;
(B) diisostearyl malate;
(C) a polyglyceryl isostearate; and
(D) a liquid oil; said process comprising:
a step of selecting the solid cosmetic base for which a layer thereof has a maximum transmittance (%) for visible light (400 to 800 nm) of a predetermined reference value or greater.

11. The solid cosmetic base according to claim 1, wherein after storing for up to 3 months in a controlled temperature at 40° C., the solid cosmetic base exhibits at least no detected exudation, separation, discoloration, or odor.

12. The solid cosmetic base according to claim 11, wherein the component (A) comprises an amide-terminated polyamide resin and/or an ester-terminated polyamide resin.

13. The solid cosmetic base according to claim 12, wherein the amide-terminated polyamide resin has the structure below

[Chem. 1]

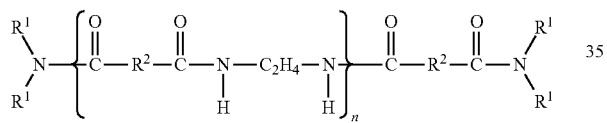

($R^1$: a straight chain or branched chain $C_8$ to $C_{22}$ alkyl group, $R^2$: a dimer acid residue or a dibasic acid residue, n=2 to 4).

14. The solid cosmetic base according to claim 11, wherein the polyglyceryl isostearate is polyglyceryl-2 diisostearate.

15. The solid cosmetic base according to claim 11, wherein the liquid oil has a viscosity at 25° C. of 5 to 400 mPa·s and is one or more selected from a saturated liquid ester oil having a branched chain, squalane, and a hydrogenated polyisobutene.

16. The solid cosmetic base according to claim 11, wherein the polyamide resin, diisostearyl malate, the polyglyceryl isostearate, and the liquid oil are contained at 5 to 50 mass %, 3 to 60 mass %, 3 to 60 mass %, and 3 to 60 mass % respectively.

17. The solid cosmetic base according to claim 11, wherein the content ratio of diisostearyl malate to the polyglyceryl isostearate is 1:5 to 5:1.

18. A solid cosmetic comprising the solid cosmetic base according to claim 11, and at least one component selected from the group consisting of a natural colorant, an oil-soluble dye, and a water-soluble dye.

19. A solid cosmetic comprising the solid cosmetic base according to claim 11.

20. A process for producing a solid cosmetic base, said solid cosmetic base consisting essentially of components (A), (B), (C), and (D) below:
(A) a polyamide resin;
(B) diisostearyl malate;
(C) a polyglyceryl isostearate; and
(D) a liquid oil; and the solid cosmetic base exhibits at least no detected exudation, separation, discoloration, or odor after storing for up to 3 months in a controlled temperature at 40° C., said process comprising:
a step of selecting the solid cosmetic for which a layer thereof has a maximum transmittance (%) for visible light (400 to 800 nm) of a predetermined reference value or greater.

* * * * *

UNITED STATES PATENT AND TRADEMARK OFFICE
CERTIFICATE OF CORRECTION

PATENT NO. : 7,993,662 B2
APPLICATION NO. : 11/453054
DATED : August 9, 2011
INVENTOR(S) : Mari Yoshida et al.

Page 1 of 2

It is certified that error appears in the above-identified patent and that said Letters Patent is hereby corrected as shown below:

Column 12, line 19 to column 13, line 13, Table 3 should appear as follows (continued next page):

TABLE 3

| Product name | Abbreviation | INCI name | Viscosity (mPa·s/25°C.) | Supplier |
|---|---|---|---|---|
| HAIMALATE DIS | DIS | Diisostearyl malate | 2830 | *1 |
| RISOREX PGIS21 | PGIS21 | Polyglyceryl-2 isostearate | 2430 | *1 |
| RISOREX PGIS22 | PGIS22 | Polyglyceryl-2 diisostearate | 700 | *1 |
| RISOREX PGIS23 | PGIS23 | Polyglyceryl-2 triisostearate | 330 | *1 |
| RISOREX PGIS24 | PGIS24 | Polyglyceryl-2 tetraisostearate | 300 | *1 |
| RISOREX PGIS32 | PGIS32 | Polyglyceryl-3 diisostearate | 3230 | *1 |
| KAK 98 | KAK 98 | Isononyl ethylhexanoate | 5 | *1 |
| KAK 99 | KAK 99 | Isononyl isononanoate | 6 | *1 |
| IPIS | IPIS | Isopropyl isostearate | 10 | *1 |
| ICEH | ICEH | Hexyldecyl ethylhexanoate | 11 | *1 |
| KAK 139 | KAK 139 | Isotridecyl isononanoate | 12 | *1 |
| KAK NDO | NDO | Neopentylglycol diethylhexanoate | 13 | *1 |
| CEH | CEH | Cetyl ethylhexanoate | 13 | *1 |
| NEOLIGHT 200P | 200P | Octyldodecyl neopentanoate | 15 | *1 |
| TOG | TOG | Triethylhexanoin | 35 | *1 |
| ISIS | ISIS | Isostearyl isostearate | 40 | *1 |

Signed and Sealed this

Thirteenth Day of December, 2011

David J. Kappos
*Director of the United States Patent and Trademark Office*

CERTIFICATE OF CORRECTION (continued)
U.S. Pat. No. 7,993,662 B2

Column 12, line 19 to column 13, line 13, Table 3 should appear as follows (continued from prior page):

| Product name | Abbreviation | INCI name | Viscosity (mPa·s/25°C.) | Supplier |
|---|---|---|---|---|
| KAK TTO | TTO | Trimethylolpropane triethylhexanoate | 52 | *1 |
| RISOCAST IOHS | IOHS | Ethylhexyl hydroxystearate | 64 | *1 |
| RISONOL 24SP | 24SP | Decyltetradecanol | 80 | *1 |
| RISONOL 28SP | 28SP | Dodecylhexadecanol | 40* | *1 |
| RISOCAST ODSHS | ODSHS | Octyldodecyl stearoyloxystearate | 90 | *1 |
| KAK PTO | PTO | Pentaerythrityl tetraethylhexanoate | 110 | *1 |
| KAK TTI | TTI | Trimethylolpropane triisostearate | 180 | *1 |
| TISG | TISG | Triisostearin | 185 | *1 |
| KAK PTI | PTI | Pentaerythrityl tetraisostearate | 290 | *1 |
| KAK DADIP-R | DADIP-R | Diisopropyl dilinoleate | 310 | *1 |
| RISOCAST MIS | MIS | Hydrogenated castor oil isostearate | 950** | *1 |
| RISOCAST DA-L | DA-L | Hydrogenated castor oil dimer dilinoleate | 1400** | *1 |
| HAILUCENT ISDA | ISDA | (Polyglyceryl-2 isostearate/dimer dilinoleate) copolymer | 2500-3500** | *1 |
| OLIVE SQUALANE | SQ | Squalane | 30 | *1 |
| Parleam 18 | PB | Hydrogenated polyisobutene | 340*** | *2 |
| E-mix D | VE | Tocopherol | | *3 |
| DC glitter gold I | Glitter G | (PET/Al/epoxy resin) laminate, iron oxide | | *4 |
| DC glitter silver C | Glitter S | (PET/Al/epoxy resin) laminate | | *4 |

HAILUCENT ISDA is a condensate formed from dimer acid, isostearic acid, and diglycerol described in JP, A, 2005-179377, and is an oligomer having a number-average molecular weight of 2000 to 7000 and a hydroxyl group value of 40 to 60.
Viscosity measurement temperature ... *: 40°C., : 60°C., *: 100°C.
Supplier ... *1: Kokyu Alcohol Kogyo Co., Ltd., *2: NOF Corporation, *3: Eisai Co., Ltd., *4: Diachemco Co., Ltd.